United States Patent
Witcher et al.

(10) Patent No.: US 11,421,261 B2
(45) Date of Patent: Aug. 23, 2022

(54) METHODS TO DETECT MICROORGANISMS

(71) Applicant: 3M INNOVATIVE PROPERTIES COMPANY, St. Paul, MN (US)

(72) Inventors: Kelvin J. Witcher, Hudson, WI (US); Francois Ahimou, Woodbury, MN (US); Naiyong Jing, St. Paul, MN (US); Tonya D. Bonilla, Woodbury, MN (US); Joshua D. Erickson, Champlin, MN (US); Hsi-Chou Liu, Woodbury, MN (US); Andrew W. Vail, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 85 days.

(21) Appl. No.: 15/733,271

(22) PCT Filed: Dec. 17, 2018

(86) PCT No.: PCT/IB2018/060204
§ 371 (c)(1),
(2) Date: Jun. 19, 2020

(87) PCT Pub. No.: WO2019/123217
PCT Pub. Date: Jun. 27, 2019

(65) Prior Publication Data
US 2020/0385778 A1   Dec. 10, 2020

Related U.S. Application Data

(60) Provisional application No. 62/607,682, filed on Dec. 19, 2017.

(51) Int. Cl.
*C12Q 1/22* (2006.01)
*C12Q 1/34* (2006.01)

(52) U.S. Cl.
CPC .............. *C12Q 1/22* (2013.01); *C12Q 1/34* (2013.01)

(58) Field of Classification Search
CPC .................................... C12Q 1/34; C12Q 1/22
See application file for complete search history.

(56) References Cited

U.S. PATENT DOCUMENTS

| | | | |
|---|---|---|---|
| 9,322,046 | B2 | 4/2016 | Chandrapati |
| 2010/0155323 | A1 | 6/2010 | Weiss |
| 2011/0201078 | A1 | 8/2011 | Rasmussen |

FOREIGN PATENT DOCUMENTS

| | | |
|---|---|---|
| JP | 2007-007575 | 1/2018 |
| WO | WO 2009-086347 | 7/2009 |
| WO | WO 2012-092242 | 7/2012 |
| WO | WO 2013-162695 | 10/2013 |
| WO | WO 2013-184366 | 12/2013 |
| WO | WO 2014-209798 | 12/2014 |
| WO | WO 2018-125798 | 7/2018 |

OTHER PUBLICATIONS

Onda et al, JP2007007575A (WIPO English Translation)—"Microorganism Carrier and Its Production Method" (translated sections—BIB data, Abstract, Description and claims). (Year: 2007).*
Albert H. et al., "Biological indicators for steam sterilization: characterization of a rapid biological indicator utilizing Bacillus stearothermophilus spore-associated alpha-glucosidase enzyme", Journal of Applied Microbiology, (1998), vol. 85, pp. 865-874. (Year: 1998).*
Li, "Nanoparticle-enhanced fluorescence emission for non-separation assays of carbohydrates using a boronic acid-alizarin complex", Chem. Commun., 2016, vol. 52, pp. 3701-3704.
Xu, "Enhanced fluorescence emission from core-shell mesoporous silica nanoparticles with amine-functionalized silica as cores", Current Nanoscience, 2012, vol. 8, No. 5, pp. 726-731.
Yamaguchi, "Acid-Base Equilibria inside Amine-Functionalized Mesoporous Silica", Analytical Chemistry, 2011, vol. 83, No. 8, pp. 2939-2946.
International Search report for PCT International Application No. PCT/IB2018/060204 dated Mar. 19, 2019, 5 pages.

* cited by examiner

*Primary Examiner* — Satyendra K Singh
(74) *Attorney, Agent, or Firm* — Qiang Han

(57) ABSTRACT

A method is provided. The method includes providing an article, the article including a nonwoven substrate having a copolymer grafted thereto, the copolymer including interpolymerized monomer units of a quaternary ammonium-containing ligand monomers; an amide monomer; an oxy monomer; and a coating on the nonwoven substrate, the coating including a plurality of test microorganisms, an enzyme or a second substrate; and contacting the article with a detection medium for a period of time.

13 Claims, 1 Drawing Sheet

METHODS TO DETECT MICROORGANISMS

BACKGROUND

Biological indicators used to determine the efficacy of sterilization are well known in the art. Rapid readout biological indicators provide a result in less time compared to their conventional counterparts. The rapid readout is often based on the detection of specific enzyme activities from the test microorganism that correlate with the loss or maintenance of spore viability post-sterilization, which can provide results for the customer within minutes to hours instead of days (conventional growth-based detection) The enzyme activities are often detected using a fluorogenic enzyme substrate where the converted substrate produces a fluorescent compound, that when excited, emits light at a specific wavelength.

SUMMARY

The present disclosure generally relates to methods for detecting microorganisms. In one aspect, the present disclosure provides a method, comprising: providing an article, the article comprising a nonwoven substrate having a copolymer grafted thereto, the copolymer comprising interpolymerized monomer units of a quaternary ammonium-containing ligand monomers; an amide monomer; an oxy monomer; and a coating on the nonwoven substrate, the coating comprising a plurality of test microorganisms, an enzyme or a second substrate; and contacting the article with a detection medium for a period of time.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, "a" nonwoven substrate can be interpreted to mean "one or more" nonwoven substrates.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The features and advantages of the present invention will be understood upon consideration of the detailed description of the preferred embodiment as well as the appended claims. These and other features and advantages of the invention may be described below in connection with various illustrative embodiments of the invention.

The above summary of the present invention is not intended to describe each disclosed embodiment or every implementation of the present invention. The Figures and the detailed description which follow more particularly exemplify illustrative embodiments. Other features, objects and advantages will become apparent from the description and drawings, and from the claims.

DETAILED DESCRIPTION

Before any embodiments of the present disclosure are explained in detail, it is understood that the invention is not limited in its application to the details of use, construction, and the arrangement of components set forth in the following description. The invention is capable of other embodiments and of being practiced or of being carried out in various ways that will become apparent to a person of ordinary skill in the art upon reading the present disclosure. Also, it is understood that the phraseology and terminology used herein is for the purpose of description and should not be regarded as limiting. The use of "including," "comprising," or "having" and variations thereof herein is meant to encompass the items listed thereafter and equivalents thereof as well as additional items. It is understood that other embodiments may be utilized and structural or logical changes may be made without departing from the scope of the present disclosure.

The present disclosure generally relates to methods that may be used to detect microorganisms such as bacteria and fungi. In particular, the present disclosure relates to methods comprising providing a nonwoven carrier with a composition of microorganisms disposed in a polymer matrix coated thereon. Advantageously, the method can significantly increase the reaction velocity (speed of the reaction and/or detection) when in combination with pH 6 or pH 7 detection media and decrease time to maximum fluorescence. Accordingly, the method can be used to rapidly detect bacteria.

Figure 1:
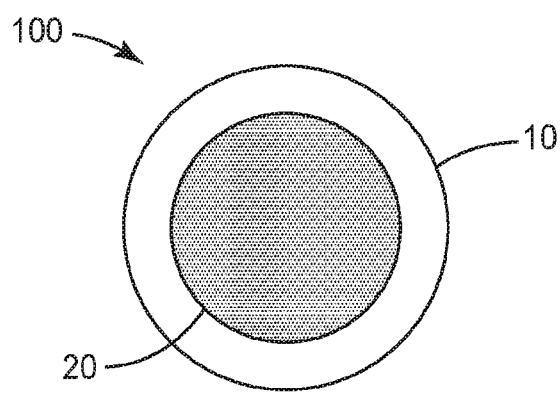
FIG. 1 is a plan view of one embodiment of an article according to the present disclosure.
Figure 2:
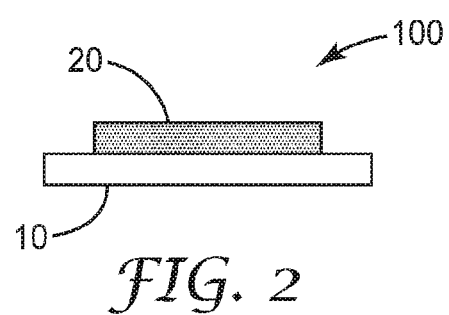
FIG. 2 is a side view of the article of FIG. 1.

The method can be used to detect microorganisms. The method can include a step of providing an article 100, and a step of contacting the article with a detection medium for a period of time. FIGS. 1 and 2 show various views of one embodiment of an article 100. The article 100 comprises a substrate 10 and a coating 20 adhered on the substrate. In any embodiment, the substrate 10 can be a sheet-like material. An example of a suitable sheet-like material for the substrate 10 is a nonwoven fabric such as, for example, a nonwoven fabric comprising meltblown fibers (e.g., meltblown fibers of a hydrophobic thermoplastic olefin).

In any embodiment wherein the substrate is a nonwoven substrate, the nonwoven substrate has a surface area of about 15 to 50 $m^2$ per square meter of nonwoven substrate. In any embodiment wherein the substrate is a nonwoven substrate, the nonwoven substrate has a solidity of less than 20%.

In any embodiment wherein the substrate is a nonwoven substrate comprising meltblown microfibers, the substrate can have a copolymer (not shown) grafted thereto. The copolymer can comprise interpolymerized monomer units of a cationic nitrogen-containing ligand monomer selected from primary ammonium-containing, secondary ammonium-containing, tertiary ammonium-containing, and/or quaternary ammonium-containing ligand monomers, an amide monomer, and an oxy monomer. Suitable nonwoven polymers having a copolymer grafted thereto are described in International Publication No. WO 2013/162695 entitled "Nonwoven Article Grafted with Copolymer", which is incorporated herein by reference in its entirety. Suitable monomer units for producing the grafted copolymers used to make the article of the present disclosure are also described in International Publication No. WO 2013/162695

In any embodiment, the grafted copolymer can comprise about 10 to 50 parts by weight of the cationic nitrogen-containing ligand monomer, about 10 to 80 parts by weight of the amide monomer, and about 10 to 40 parts by weight of the oxy monomer. Optionally, the grafted copolymer can comprise about 0 to 30 parts by weight of a poly(alkylene oxide) monomer. The sum of the portions of each of the aforementioned monomers is 100 parts by weight. In any embodiment, the weight of the grafted polymer can be 0.5 to 5 times the weight of the nonwoven substrate. In any embodiment wherein the polymer comprises poly(alkylene oxide), wherein the poly(alkylene oxide) has a weight average molecular weight of 20,000 Daltons.

The polymer grafted article comprises a nonwoven substrate, and a grafted copolymer comprising interpolymerized monomer units of a) a cationic nitrogen-containing ligand monomer; b) an amide monomer, and c) an "oxy" monomer. The cationic nitrogen-containing ligand monomer includes primary ammonium-containing, secondary ammonium-containing, tertiary ammonium-containing and quaternary ammonium-containing ligand monomers. The "oxy" monomer is inclusive of epoxy monomers and $C_3$-$C_{10}$, preferably $C_4$-$C_6$, monoether-containing monomers. More specifically, the grafted copolymer comprises interpolymerized monomer units including a. 10 to 50 parts by weight of the cationic nitrogen-containing ligand monomer;
10 to 80 parts by weight of the amide monomer, and
10 to 40 parts by weight of the oxy monomer; and
wherein the sum of a to c is 100 parts by weight.

The cationic nitrogen-containing ligand monomer is of the general formula:

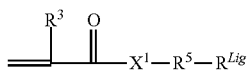

I where $X^1$ is —O— or —$NR^3$—, $R^3$ is H or $C_1$-$C_4$ alkyl-; $R^5$ is an (hetero)hydrocarbyl group, preferably a hydrocarbyl group, more preferably a $C_1$-$C_8$ alkylene, and $R^{Lig}$ is a quaternary ammonium ligand group.

In any embodiment, the cationic nitrogen-containing ligand monomer is a quaternary ammonium monomer is of the general formula:

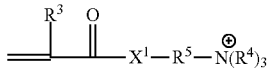

II where $X^1$ is —O— or —$NR^3$—, where each $R^3$ is H or $C_1$-$C_4$ alkyl, preferably H or methyl; and $R^5$ is an alkylene (e.g., an alkylene having 1 to 10 carbon atoms, 1 to 6, or 1 to 4 carbon atoms), each $R^4$ is independently hydrogen, alkyl, or aryl and may be substituted by a hydroxyl group. The counter ions of the quaternary ammonium salts are often halides, sulfates, phosphates, nitrates, and the like. Such monomers having a quaternary ammonium group preferably may be directly grafted to the surface of the nonwoven substrate (in the presence of the additional co-monomers described herein), or less preferably an aminoalkyl (meth) acryloyl monomer having a primary, secondary or tertiary amine group, may be grafted and subsequently converted by alkylation to a quaternary ammonium group of Formula II.

Useful aminoalkyl (meth)acrylates (i.e., in Formula II is oxy) can include di alkylaminoalkyl(meth)acrylates for example, [2-(Diethylamino)ethyl] methacrylate or [2-(Dimethylamino)ethyl] methacrylate, trialkylaminoalkyl(meth) acrylates such as, trimethylaminoethylmethacrylate, trimethylaminoethylacrylate, triethylaminoethylmethacylate, triethylaminoethylacrylate, trimethylaminopropylmethacrylate, trimethylaminopropylacrylate, dimethylbutylaminopropylmethacrylate, diethylbutylaminopropylacrylate and the like. Exemplary amino (meth)acrylamides (i.e., $X^1$ in Formula II is —$NR^3$—) include, for example, 3-(trimethylamino)propylmethacrylamide, 3-(triethylamino)propylmethacrylamide, 3-(ethyldimethylamino)propylmethacrylamide.

Suitable quaternary salts of the aminoalkyl (meth)acryloyl monomers of Formula I include, but are not limited to, (meth)acrylamidoalkyltrimethylammonium salts (e.g., 3-methacrylamidopropyltrimethylammonium chloride and 3-acrylamidopropyltrimethylammonium chloride) and (meth)acryloxyalkyltrimethylammonium salts (e.g., 2-acryloxyethyltrimethylammonium chloride, 2-methacryloxyethyltrimethylammonium chloride, 3-methacryloxy-2-hydroxypropyltrimethylammonium chloride, 3-acryloxy-2-hydroxypropyltrimethylammonium chloride, and 2-acryloxyethyltrimethylammonium methyl sulfate).

Suitable quaternary salts of the aminoalkyl (meth)acryloyl monomers of Formula I can include, but are not limited to, 2-aminoethyl methacrylate methacrylamide, 2-aminoethyl methacrylamide, N-(3-aminopropyl) methacrylamide, N-(2-aminoethyl) methacrylamide, 2-(tert-Butylamino) ethyl methacrylate, (2-Boc-amino)ethyl methacrylate, N-tert-Butyl acrylamide, N-isopropyl acrylamide, N-phenyl acrylamide, N-ethyl acrylamide, N-(2-aminoethyl) methacrylamide, N-isopropylmethacrylamide, N-(Triphenylmethyl)methacrylamide, N-(hydroxyethyl) acrylamide, N-(hydroxymethyl) acrylamide, (4-Hydroxyphenyl)methacrylamide, 2-Hydroxypropyl methacrylamide, 2-(Dimethylamino)ethyl acrylate, 3-(Dimethylamino)propyl acrylate, 2-(Diethylamino)ethyl acrylate, 3-(Dimethylamino)neopentyl acrylate, 2-N-Morpholinoethyl acrylate, 2-(Dimethylamino)ethyl methacrylate, 2-(Diethylamino)ethyl methacrylate, 2-(Diisopropylamino)ethyl methacrylate, 2-N-Morpholinoethyle methacrylate, N-(3-N,N-Dimethylamino) propyl acrylamide, N,N-Diethylacrylamide, N,N Diethylmethacrylamide, N-(2-N,N-Dimethylamino)ethyl methacrylamide, N-(3-N,N-Dimethylamino)propyl methacrylamide The grafted copolymer may comprise 10 to 50 parts by weight, preferably 20 to 40 parts by weight, of such quaternary amine monomer units, relative to 100 parts total grafting monomer(s). The grafted copolymer further comprises "oxy monomer" units which are inclusive of epoxy functional monomer units and alkyl ether functional monomer units. Desirably, the oxy monomers have an aqueous solubility of 15-25 g/L. Such "oxy monomer" include epoxy-functional and monoether-functional (meth)acrylates and (meth)acrylamides and include those of the general formula:

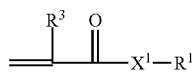

III wherein:
$R^3$ is —H or $C_1$-$C_4$ alkyl;
$X^1$ is —$NR^3$— or —O—; and
$R^1$ is an epoxy-functional or ether-functional (hetero)hydrocarbyl group. More particularly the ether functional group is a lower alkyleneoxy alkyl group. Preferably, the $R^1$ group is based on a straight-chain, branched, cyclic or polycyclic hydrocarbon of 2 to 30 carbons having an oxirane (epoxy) group included. More preferably, the $R^8$ group contains 3 to 10 carbons, such as glycidyl methacrylate (GMA).

Some preferred epoxy monomers are of the formula:

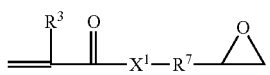
IV wherein:
$R^7$ is a (hetero)hydrocarbyl group, preferably a hydrocarbyl group, more preferably a $C_1$-$C_6$ alkylene;
$R^3$ is —H or $C_1$-$C_4$ alkyl; and
$X^1$ is —$NR^3$— or —O—.

Representative epoxy monomers include glycidyl (meth)acrylate, thioglycidyl (meth)acrylate, 3-(2,3-epoxypropoxy)phenyl (meth)acrylate, 2-[4-(2,3-epoxypropoxy)phenyl]-2-(4-(meth)acryloyloxy-phenyl)propane, 4-(2,3-epoxypropoxy)cyclohexyl (meth)acrylate, 2,3-epoxycyclohexyl (meth)acrylate, and 3,4-epoxycyclohexyl (meth)acrylate.

In one useful embodiment, the epoxy functional monomer is derived from the reaction of vinyldimethyl azlactone with a hydroxyalkyl epoxy compound as shown in Scheme 1:

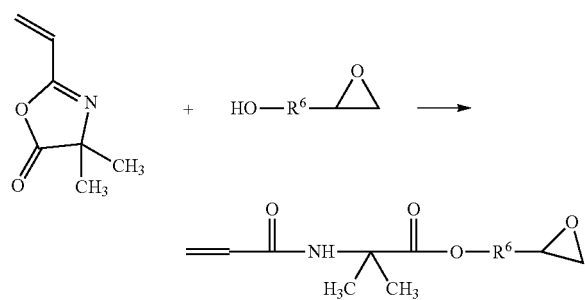

where $R^6$ is a $C_1$-$C_6$ alkylene.

It is believed that the epoxy groups of these monomers in the grafted copolymer hydrolytically ring open to provide terminal, pendent diol groups on the copolymer. Thus, the original grafted hydrophobic epoxy group hydrolyzes to provide a hydrophilic diol group to the grafted copolymer.

The "oxy monomers" alternatively may be selected from lower alkyl ether functional monomers. Such ether functional monomers comprise lower monomer ether monomers of the formula:

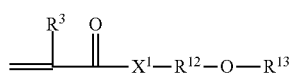
V where
$R^3$ is —H or $C_1$-$C_4$ alkyl; and
$X^1$ is —$NR^3$— or —O—,
$R^{12}$ is a linear or branched $C_2$-$C_4$ alkylene, and
$R^{13}$ is a linear or branched $C_1$-$C_4$ alkyl. Preferably the sum of the carbon atoms of the $R^{12}$ and $R^{13}$ groups is from 3 to 10, preferably 3 to 6.

The grafted copolymer may comprise 10 to 40 parts by weight, preferably 15 to 35 parts by weight, of such oxy monomer units, relative to 100 parts total grafting monomer(s).

The grafted polymer optionally contains other ethylenically-unsaturated hydrophilic amide monomer units. As used herein these "hydrophilic monomers" are those polymerizable amide monomers having a water miscibility (water in monomer) of at least 1 wt. %, preferably at least 5 weight % without reaching a cloud point. The hydrophilic amide monomer units include (meth)acrylamides and N-vinyl amides are of the general formulas:

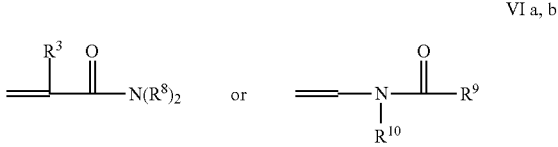
VI a, b where
$R^3$ is —H or $C_1$-$C_4$ alkyl;
Each $R^8$ is an H, an alkyl or an aryl group,
$R^9$ and $R^{10}$ are alkyl groups, or may be taken together to form a 5 or 6-membered ring.

Examples of suitable hydrophilic monomers include N-vinyl caprolactam, N-vinyl acetamide, N-vinyl pyrrolidone, acrylamide, mono- or di-N-alkyl substituted acrylamide, and combinations thereof. Preferred polar monomers include N-vinyl pyrrolidone, N-vinyl acetamide, methylacrylamide, and mixtures thereof.

The grafted copolymer may comprise 10 to 80 parts by weight, preferably 30 to 60 parts by weight, of such amide monomer units, relative to 100 parts total grafting monomer(s).

In some preferred embodiments, the quaternary ammonium-containing monomer used to make the copolymer comprises [2-(Diethylamino)ethyl] methacrylate or [2-(Dimethylamino)ethyl] methacrylate. In some preferred embodiments, the quaternary ammonium-containing monomer used to make the copolymer comprises [2-(Methacryloyloxy)ethyl] trimethylammonium chloride or [3-(Methacryloylamino)propyl]trimethylammonium chloride. In some preferred embodiments, the oxy monomer used to make the copolymer comprises glycidyl methacrylate. In some preferred embodiments, the amide monomer used to make the copolymer comprises N-vinyl pyrrolidone. In a preferred embodiment, the quaternary ammonium-containing monomer used to make the copolymer comprises [3-(Methacryloylamino)propyl]trimethylammonium chloride, the oxy monomer used to make the copolymer comprises glycidyl methacrylate, and the amide monomer used to make the copolymer comprises N-vinyl pyrrolidone. In a preferred embodiment, the quaternary ammonium-containing monomer used to make the copolymer comprises [2-(Diethylamino)ethyl methacrylate, the oxy monomer used to make the copolymer comprises glycidyl methacrylate, and the amide monomer used to make the copolymer comprises N-vinyl pyrrolidone.

In any embodiment, the quaternary ammonium-containing monomer and the oxy monomer used to make the copolymer each comprises a monomer selected from the group consisting of an acrylate monomer, a methacrylate monomer, an acrylamide monomer, and a methacrylamide monomer. In any of these embodiments, the amide monomer is selected from the group consisting of an acrylamide monomer, a methacrylamide monomer, and an N-vinylamide monomer.

In any embodiment, the oxy monomer used to make the copolymer comprises a monomer selected from the group consisting of an acrylate monomer, a methacrylate monomer, an acrylamide monomer, and a methacrylamide monomer with an epoxy substituent.

With regard to the grafting monomers supra, the monomers that are grafted to the surface of the nonwoven substrates usually have either an acrylate or other non-acrylate polymerizable functional group for grafting by e-beam.

The coating 20 can include a plurality of test microorganisms (e.g., bacterial spores), an enzyme or a second substrate. The test microorganisms (e.g., bacterial spores) comprise, and/or are capable of producing, a detectable biological activity (e.g., an enzyme activity). In any embodiment wherein the test microorganisms are spores, the spores in the coating 20 can be viable spores (i.e., capable of biological activities such as germination and/or binary fission (after germination)).

When producing an article according to the present disclosure, the test microorganisms can be suspended in a suitable suspending liquid (e.g., water, a buffered aqueous solution, a hydrogel). A hydrogel can be formed from a polymer solution, for example, by a temperature change or upon dry down. The hydrogel is produced, for example, as a result of the formation of hydrogen bonds, or by crystallization, or by other polymer-polymer interactions. The concentration of test microorganisms in the suspending liquid or the hydrogel can be adjusted so that applying a predetermined volume of the suspending liquid to the substrate results in the delivery of a predetermined number of test microorganisms onto the substrate. The predetermined number of viable test microorganisms on the article can be about 10 test microorganisms, about 100 test microorganisms, about $10^3$ test microorganisms, about $10^4$ test microorganisms, about $10^5$ test microorganisms, about $10^6$ test microorganisms, about $10^7$ test microorganisms or about $10^8$ test microorganisms.

After suspending the test microorganisms (e.g., spores) in the suspending liquid, the predetermined volume of suspending liquid can be deposited (e.g., by pipet) onto the substrate. The coating can migrate into voids in the surface of the substrate.

The test microorganisms can be any suitable test microorganisms. Suitable test microorganisms include endospore (spore)-forming bacteria (e.g., a species of the genus *Geobacillus* or *Bacillus*), bacteria (e.g. a species from the genus *Mycobacterium*) and fungal spores (e.g. a species of the genus *Aspergillus*) that are known in the art. In any embodiment wherein the test microorganisms are spores, the spores used in the coating 20 can comprise spores of a species of spore-forming bacteria. In any embodiment, the spore-forming bacteria can comprise spores of a species of *Geobacillus, Bacillus* or *Clostridium*. In any embodiment, the spores of a species of *Geobacillus, Bacillus* or *Clostridium* can comprise spores of *Geobacillus stearothermophilus, Bacillus atrophaeus, Bacillus subtilis, Clostridium sporogenes, Geobacillus thermoglucosidasius, Geobacillus kaustophilis*.

The enzyme can be any suitable enzyme, for example, α-glucosidase, α-galactosidase, lipase, esterase, acid phosphatase, alkaline phosphatase, proteases, aminopeptidase, chymotrypsin, β-glucosidase, β-galactosidase, α-glucoronidase, β-glucoronidase, phosphohydrolase, plasmin, thrombin, trypsin, calpain, α-mannosidase, β-mannosidase, α-L-fucosidase, leucine aminopeptidase, a-L-arabinofuranoside, cysteine aminopeptidase, valine aminopeptidase, β-xylosidase, α-L-iduronidase, glucanase, cellobioside, cellulase, α-arabinosidase, glycanase, sulfatase, butyrate, glycosidase, arabinoside.

The second substrate can be any suitable substrate. The second substrate can be an enzyme substrate or converted enzyme substrate. The second substrate can be for example, derivatives of 4-methylumbeltiferyl including: 4-Methylumbelliferyl α-D-glucopyranoside, 4-methylumbelliferyl α-D-galactopyranoside, 4-methylumbelliferyl heptanoate, 4-methylumbelliferyl palmitate, 4-methylumbelliferyl oleate, 4-methylumbelliferyl acetate, 4-metbylumbelliferyl-nonanoate, 4-methylumbelliferyl caprylate, 4-methylumbelliferyl butyrate, 4-methylumbelliferyl-beta-D-cellobioside, 4-methylumbelliferyl acetate; 4-methylumbelliferyl phosphate; 4-methylumbelliferyl sulfate 4-methylumbelliferyl-beta-trimethylammonium cinnamate chloride; 4-methylumbelliferyl-beta-D-N, N',N''-triacetylchitotriose; 4-methylumbelliferyl-beta-D-xyloside, 4-methylumbelliferyl-N-acetyl-beta-D-glucosaminide, 4-methylumbelliferyl-N-acetyl-alpha-D-glucosaminide, 4-methylumbelliferyl propionate; 4-methylumbelliferyl stearate, 4-methylumbelliferyl-alpha-L-arabinofuranoside; 4-methylumbelliferyl alpha-L-arabinoside; methylumbelliferyl-beta-D-N,N'-diacetyl chitobioside; 4-methylumbelliferyl elaidate; 4-methylumbelliferyl-alpha-D-mannopyranoside; 4-methylumbelliferyl-beta-D-mannopyranoside; 4-methylumbelliferyl-beta-D-fucoside 4-methylumbelliferyl-alpha-L-fucoside; 4-methylumbelliferyl-beta-L-fucoside, 4-methylumbelliferyl-alpha-D-galactoside; 4-methylumbelliferyl-beta-D-galactoside; 4-trifluoromethylumbelliferyl beta-D-galactoside; 4-methylumbelliferyl-alpha-D-glucoside; 4-methylumbelliferyl-beta-D-glucoside; 4-methylumbelliferyl-7,6-sulfo-2-acetamido-2-deoxy-beta-D-glucoside; 4-methylumbelliferyl-beta-D-glucuronide; 6,8-difluor-4-methylumbelliferyl-beta-D-glucuronide, 6,8-difluoro-4-methylumbelliferyl-beta-D-galactoside, 6,8-Difluoro-4-Methylumbelliferyl Phosphate, 6,8-difluoro-4-methylumbelliferyl beta-D-xylobioside. The second substrate can also be derivatives of 7-amido-4-methyl-coumarin, including: Ala-Ala-Phe-7-amido-4-methylcoumarin, Boc-Gln-Ala-Arg-7-amido-4-methylcoumarin hydrochloride, Boc-Leu-Ser-Thr-Arg-7-amido-4-methylcoumarin, Boc-Val-Pro-Arg-7-amido-4-methylcoumarin hydrochloride, D-Ala-Leu-Lys-7-amido-4-methylcoumarin, L-Alanine 7-amido-4-methylcoumarin trifluoroacetate salt, L-Methionine 7-amido-4-methylcoumarin trifluoroacetate salt, L-Tyrosine 7-amido-4-methylcoumarin, Lys-Ala-7-amido-4-methylcoumarin dihydrochloride, N-p-Tosyl-Gly-Pro-Arg 7-amido-4-methylcoumarin hydrochloride, N-Succinyl-Ala-Ala-Phe-7-amido-4-methylcoumarin, N-Succinyl-Ala-Ala-Pro-Phe-7-amido-4-methylcoumarin, N-Succinyl-Ala-Phe-Lys 7-amido-4-methylcoumarin acetate salt, N-Succinyl-Leu-Leu-Val-Tyr-7-Amido-4-Methylcoumarin, D-Val-Leu-Lys 7-amido-4-methylcoumarin, Fmoc-L-glutamic acid 1-(7-amido-4-methylcoumarin), Gly-Pro-7-amido-4-methylcoumarin hydrobromide, L-Leucine-7-amido-4-methylcoumarin hydrochloride, L-Proline-7-amido-4-methylcoumarin hydrobromide, diacetylfluorescein derivatives; and fluorescamine.

The detection medium can comprise one or more reagent. In any embodiment, the reagent can be dissolved or suspended in an aqueous medium (e.g., water, an aqueous buffer). In any embodiment, the reagent may be an effective amount of a nutrient that facilitates germination and/or growth of the test microorganism (e.g. spores). Non-limiting examples of suitable nutrients include L-alanine, L-valine, L-asparagine, L-tyrosine, inosine, peptones, tryptones, soytones, dextrose, sucrose, maltose, glycogen, trehalose, sodium chloride serine, proline, arginine, glutamate, asparagine, aspartate, threonine, lipids, fatty acids, potato infusion, yeast extract, malt extract, peptones, dextrose, and a combination of any two or more of the foregoing nutrients. Alternatively, or additionally, the reagent may be an indicator compound facilitates detection of a metabolic activity of the test microorganism (e.g., spore). In any embodiment, the metabolic activity can be an enzyme activity. Non-limiting examples of indicator compounds include a chromogenic enzyme substrate, a fluorogenic enzyme substrate, a pH indicator, a redox indicator, a chemiluminescent enzyme substrate, a dye, and a combination of any two or more of the foregoing indicator compounds.

After contacting the article with an effective amount of the detection medium, the method comprises the step of analyzing the detection medium to detect test microorganisms. Detection of test microorganisms can be performed using any of a variety of microorganism detection techniques that are known in the art including, for example, detection of spore germination, detection of microorganism growth, detection of microorganism reproduction, detection of biological activity of a microorganism, for example a metabolic activity (e.g., an enzyme activity, fermentation of a nutrient, an oxidation/reduction reaction), and a combination of any two or more of the foregoing detection techniques. In any embodiment, contacting the article with the detection medium for a period of time can comprise contacting the article with the detection medium at a predefined temperature that facilitates a metabolic activity of the test microorganisms (e.g., the article can be incubated at a temperature suitable for growth and/or enzyme activity of the test microorganism).

In any embodiment of any of the methods of the present disclosure wherein the test microorganisms comprise spores, analyzing the detection medium to detect a biological activity of the test microorganisms comprises detecting vegetative cells derived from germination and/or outgrowth of the spores.

In any embodiment of any of the methods of the present disclosure wherein the test microorganisms comprise spores, analyzing the detection medium to detect a biological activity of the test microorganisms comprises detecting an enzyme activity of the spores and/or an enzyme activity of vegetative cells derived from germination and/or outgrowth of the spores. In any embodiment, detecting an enzyme activity comprises detecting an enzyme activity selected from the list of beta-D-galactosidase, beta-D-glucosidase, alpha-D-glucosidase, alkaline phosphatase, acid phosphatase, butyrate esterase, caprylate esterase lipase, chloroamphenicol acetytransferase, catechol-2,3-dioxygenase, myristate lipase, leucine am inopeptidase, valine aminopeptidase, chymotrypsin, phosphohydrolase, alpha-D-galactosidase, alpha-L-arabinofuranosidase, N-acetyl-beta-glucosaminidase, beta-D-cellobiosidase, alanine aminopeptidase, proline aminopeptidase, tyrosine aminopeptidase, phenylalanine aminopeptidase, beta-D-glucuronidase, fatty acid esterase, and a combination of any two or more of the foregoing enzyme.

Analyzing the detection medium can comprise determining whether an indicator compound changed from a first state to a second state. Analyzing the detection medium can comprise visually observing the detection medium for a visible change from a first state to a second state. Alternatively, or additionally, analyzing the detection medium can comprise placing the detection medium into an instrument to analyze the detection medium for a change from a first state to a second state. In any embodiment, analyzing the detection medium can comprise comparing the detection medium and/or comparing the detection medium to "control". Analyzing the detection medium to detect a biological activity of the test microorganisms can comprise analyzing the detection medium at a pH between 5 and 9, between 6 and 9, between 7 and 9, between 6 and 8, or between 7 and 8. Analyzing the detection medium at these pH values can avoid adding sodium carbonate at the end of the assay to raise the pH to >10 for detection, thus decrease the detection time.

In any embodiment of any of the methods of the present disclosure, contacting the article with the detection medium for a period of time comprises contacting the article with the detection medium at a predefined temperature. The predefined temperature may vary according to the test microorganism. Suitable predefined temperatures may include temperatures in the range from about 20 degrees C. to about 80 degrees C., for example. In any embodiment of any of the methods of the present disclosure, contacting the article with the detection medium for a period of time comprises contacting the article with the detection medium at a pH between 5 and 9.

The following embodiments are intended to be illustrative of the present disclosure and not limiting.

Embodiments

Embodiment 1 is a method, comprising: providing an article, the article comprising a nonwoven substrate having a copolymer grafted thereto, the copolymer comprising interpolymerized monomer units of a quaternary ammonium-containing ligand monomers; an amide monomer; an oxy monomer; and a coating on the nonwoven substrate, the coating comprising a plurality of test microorganisms, an enzyme or a second substrate; and contacting the article with a detection medium for a period of time.

Embodiment 2 is the method of embodiment 1, wherein the coating comprises a plurality of test microorganisms and the method further comprising after contacting the article with the detection medium for a period of time, analyzing the detection medium to detect a biological activity of the test microorganisms.

Embodiment 3 is the method of embodiment 2, wherein analyzing the detection medium to detect a biological activity of the test microorganisms comprises detecting an enzyme activity of the spores and/or an enzyme activity of vegetative cells derived from germination and/or outgrowth of a spore.

Embodiment 4 is the method of embodiment 3, wherein detecting the enzyme activity comprises detecting an enzyme activity selected from the list of consisting of beta-D-galactosidase, beta-D-glucosidase, alpha-D-glucosidase, alkaline phosphatase, acid phosphatase, butyrate esterase, caprylate esterase lipase, chloroamphenicol acetytransferase, catechol-2,3-dioxygenase, myristate lipase, leucine aminopeptidase, valine aminopeptidase, chymotrypsin, phosphohydrolase, alpha-D-galactosidase, alpha-L-arabinofuranosidase, N-acetyl-beta-glucosaminidase, beta-D-cellobiosidase, alanine aminopeptidase, proline aminopeptidase, tyrosine aminopeptidase, phenylalanine aminopeptidase, beta-D-glucuronidase, fatty acid esterase, and a combination of any two or more of the foregoing enzyme.

Embodiment 5 is the method of any one of embodiments 2-4, wherein analyzing the detection medium to detect a biological activity of the test microorganisms comprises analyzing the detection medium at a pH between 5 and 9.

Embodiment 6 is the method of any one of embodiments 2-5, wherein analyzing the detection medium to detect a biological activity of the test microorganisms comprises analyzing the detection medium at a pH between 6 and 8.

Embodiment 7 is the method of any one of embodiments 1-6, wherein contacting the article with the detection medium for a period of time comprises contacting the article with the detection medium at a predefined temperature.

Embodiment 8 is the method of any one of embodiments 1-7, wherein contacting the article with the detection medium for a period of time comprises contacting the article with the detection medium at a pH between 5 and 9.

Embodiment 9 is the method of any one of embodiments 1-8, wherein the detection medium can comprise a reagent selected from the group consisting of an effective amount of a nutrient that facilitates germination and/or growth of the test microorganisms, an indicator compound facilitates detection of a test microorganism metabolic activity, and a combination of any two or more of the foregoing reagents.

Embodiment 10 is the method of any one of embodiments 1-9, wherein the indicator compound is selected from the group consisting of a chromogenic enzyme substrate, a fluorogenic enzyme substrate, a pH indicator, a redox indicator, a chemiluminescent enzyme substrate, a dye, and a combination of any two or more of the foregoing indicator compounds.

Embodiment 11 is the method of any one of embodiments 1-10, wherein the test microorganisms comprise spores.

Embodiment 12 is the method of embodiment 11, wherein the spores comprise spores of a species of bacterial spores.

Embodiment 13 is the method of any one of embodiments 1-12, wherein the quaternary ammonium-containing monomer used to make the copolymer comprises [2-(Diethylamino)ethyl] methacrylate or [2-(Dimethylamino)ethyl] methacrylate.

Embodiment 14 is the method of any one of embodiments 1-13, wherein the enzyme comprises α-glucosidase.

Embodiment 15 is the method of any one of embodiments 1-14, wherein the second substrate comprises 4-Methylumbelliferyl α-D-glucopyranoside.

The following working examples are intended to be illustrative of the present disclosure and not limiting.

Example 1

A 17.8 cm by 17.8 cm sheet of polypropylene blown microfiber nonwoven substrate [Total Polypropylene 3860X resin (Total Petrochemicals, Inc., Houston, Tex.), basis weight of 99 grams per square meter, effective fiber diameter of 6.1 microns, solidity of 7.9%] was cut and weighed. An imbibing solution was prepared by mixing 2-aminoethyl methacrylate hydrochloride (1.41 g) with N-vinyl-2-pyrrolidone (6.28 g) and glycidyl methacrylate (2.05 g) in 25 g of deionized water. The mixture was diluted to 50 g by adding deionized water. The substrate sheet and the vessel containing the imbibing solution were each placed in an oxygen depleted (<50 PEm $O_2$) glovebox that was purged with nitrogen. The sheet was transferred to a plastic bag and sealed. The sealed bag was then removed from the glove box and irradiated to a dose level of 70 kGy by passing through an Energy Sciences, Inc. 'Electrocurtain' CB-300 electron beam in a single pass operation at a web speed of approximately 5.5 meters/minute and an accelerating voltage of 300 kV. The sealed bag was returned to the nitrogen atmosphere controlled glove box. The bag was opened and the nonwoven material was imbibed with 30 g of the nitrogen purged imbibing solution. The bag was then resealed after expelling most of the nitrogen. A roller was used to uniformly distribute the imbibing solution to the substrate. The substrate was maintained flat in the bag for 24 hours. The resulting copolymer grafted nonwoven substrate was removed from the bag and washed with gentle agitation for 20 minutes in a bath of hot deionized water (80° C.). The wash procedure was repeated three additional times with fresh water used in each wash step. The washed sample was placed in an aluminum pan, air dried overnight at room temperature, and then sealed overnight in a plastic bag that contained Drierite brand desiccant (W. A. Hammond Drierite Company, Xenia, Ohio). The substrate material was weighed both before and after the grafting procedure to determine the amount of copolymer material grafted to the substrate. The weight of the substrate following grafting was about 247% of the original weight of the substrate.

Example 2

The grafting procedure of Example 1 was followed with the exception that the imbibing solution of Example 1 was replaced with a new imbibing solution. The new imbibing solution was prepared by mixing N-isopropylacrylamide

EXAMPLES

TABLE 1

Materials

| Description (abbreviation) | Source |
|---|---|
| 2-Aminoethyl methacrylate hydrochloride (AEMA) | Sigma-Aldrich Co., St. Louis, MO |
| N-isopropylacrylamide (IPAA) | Sigma-Aldrich Co., St. Louis, MO |
| N-(Hydroxymethyl)acrylamide (HMAA) (48 weight % in water) | Sigma-Aldrich Co., St. Louis, MO |
| 2-(Diethylamino)ethyl methacrylate (DEAEMA) | Sigma-Aldrich Co., St. Louis, MO |
| 2-(Dimethylamino)ethyl methacrylate (DMAEMA) | Sigma-Aldrich Co., St. Louis, MO |
| 2-(Dimethylamino)ethyl acrylate (DMAEA) | Sigma-Aldrich Co., St. Louis, MO |
| [2-(Methacryloyloxy)ethyl]trimethylammonium chloride (MOETAC) (80 weight % in water) | Sigma-Aldrich Co., St. Louis, MO |
| [3-(Methacryloylamino)propyl]trimethylammonium chloride (MAPTAC) (50 weight % in water) | Sigma-Aldrich Co., St. Louis, MO |
| N-vinyl-2-pyrrolidone (NVP) | Acros Organics, Geel, Belgium |
| Glycidyl methacrylate (GMA) | Alfa Aesar Co., Haverhill, MA |

(1.24 g) with N-vinyl-2-pyrrolidone (6.26 g) and glycidyl methacrylate (2.12 g) in 25 g of deionized water. The mixture was diluted to 50 g by adding deionized water. The weight of the substrate following grafting was about 306% of the original weight of the substrate.

Example 3

The grafting procedure of Example 1 was followed with the exception that the imbibing solution of Example 1 was replaced with a new imbibing solution. The new imbibing solution was prepared by mixing N-(hydroxymethyl)acrylamide (2.66 g) with N-vinyl-2-pyrrolidone (6.26 g) and glycidyl methacrylate (2.06 g) in 25 g of deionized water. The mixture was diluted to 50 g by adding deionized water. The weight of the substrate following grafting was about 317% of the original weight of the substrate.

Example 4

The grafting procedure of Example 1 was followed with the exception that the imbibing solution of Example 1 was replaced with a new imbibing solution. The new imbibing solution was prepared by mixing 2-(diethylamino)ethyl methacrylate (1.25 g) with N-vinyl-2-pyrrolidone (6.28 g) and glycidyl methacrylate (2.02 g) in 25 g of deionized water. The mixture was diluted to 50 g by adding deionized water. The weight of the substrate following grafting was about 289% of the original weight of the substrate.

Example 5

The grafting procedure of Example 1 was followed with the exception that the imbibing solution of Example 1 was replaced with a new imbibing solution. The new imbibing solution was prepared by mixing 2-(dimethylamino)ethyl methacrylate (1.25 g) with N-vinyl-2-pyrrolidone (6.25 g) and glycidyl methacrylate (2.12 g) in 25 g of deionized water. The mixture was diluted to 50 g by adding deionized water. The weight of the substrate following grafting was about 252% of the original weight of the substrate.

Example 6

The grafting procedure of Example 1 was followed with the exception that the imbibing solution of Example 1 was replaced with a new imbibing solution. The new imbibing solution was prepared by mixing 2-(dimethylamino)ethyl acrylate (1.25 g) with N-vinyl-2-pyrrolidone (6.21 g) and glycidyl methacrylate (2.01 g) in 25 g of deionized water. The mixture was diluted to 50 g by adding deionized water. The weight of the substrate following grafting was about 261% of the original weight of the substrate.

Example 7

The grafting procedure of Example 1 was followed with the exception that the imbibing solution of Example 1 was replaced with a new imbibing solution. The new imbibing solution was prepared by mixing [2-(methacryloyloxy)ethyl]trimethylammonium chloride (1.62 g) with N-vinyl-2-pyrrolidone (6.22 g) and glycidyl methacrylate (2.07 g) in 25 g of deionized water. The mixture was diluted to 50 g by adding deionized water. The weight of the substrate following grafting was about 234% of the original weight of the substrate.

Example 8

The grafting procedure of Example 1 was followed with the exception that the imbibing solution of Example 1 was replaced with a new imbibing solution. The new imbibing solution was prepared by mixing [3-(methacryloylamino)propyl]trimethylammonium chloride solution (2.50 g) with N-vinyl-2-pyrrolidone (6.25 g) and glycidyl methacrylate (2.06 g) in 25 g of deionized water. The mixture was diluted to 50 g by adding deionized water. The weight of the substrate following grafting was about 279% of the original weight of the substrate.

Comparative Example 1

A 17.8 cm by 17.8 cm sheet of polypropylene blown microfiber nonwoven substrate [Total Polypropylene 3860X resin (Total Petrochemicals, Inc., Houston, Tex.), basis weight of 99 grams per square meter, effective fiber diameter of 6.1 microns, solidity of 7.9%] was cut and weighed. An imbibing solution was prepared by mixing N-vinyl-2-pyrrolidone (6.28 g) and glycidyl methacrylate (2.06 g) in deionized water (41.66 g). The substrate sheet and the vessel containing the imbibing solution were each placed in an oxygen depleted (<50 PEm $O_2$) glovebox that was purged with nitrogen. The sheet was transferred to a plastic bag and sealed. The sealed bag was then removed from the glove box and irradiated to a dose level of 70 kGy by passing through an Energy Sciences, Inc. 'Electrocurtain' CB-300 electron beam in a single pass operation at a web speed of approximately 5.5 meters/minute and an accelerating voltage of 300 kV. The sealed bag was returned to the nitrogen atmosphere controlled glove box. The bag was opened and the nonwoven material was imbibed with 30 g of the nitrogen purged imbibing solution. The bag was then resealed after expelling most of the nitrogen. A roller was used to uniformly distribute the imbibing solution to the substrate. The substrate was maintained flat in the bag for 24 hours. The resulting copolymer grafted nonwoven substrate was removed from the bag and washed with agitation for 20 minutes in a bath of hot deionized water (80° C.). The wash procedure was repeated three additional times with fresh water used in each wash step. The washed sample was placed in an aluminum pan, air, dried overnight at room temperature, and then sealed overnight in a plastic bag that contained Drierite brand desiccant (W. A. Hammond Drierite Company). The substrate material was weighed both before and after the grafting procedure to determine the amount of copolymer material grafted to the substrate. The weight of the substrate following grafting was about 248% of the original weight of the substrate.

Example 9

A modified version of the Biological Sterilization Indicator (BI) Devices as described in the Examples Section of U.S. Pat. No. 9,322,046 were prepared (see FIGS. 1-7 and the description in the Examples Section for device dimensions). The modifications included the following changes to the device. The frangible container was replaced with the media ampoule from a commercially available 3M ATTEST Rapid Readout Biological Indicator 1295 device (3M Corporation, Maplewood, Minn.). The media ampoule contained 4-methylumbelliferyl-alpha-D-glucoside (MUG) and bromocresol purple as detection indicators. The spore reservoir contained a section of copolymer grafted nonwoven substrate selected form Examples 1-9 and Comparative Example 1 that was coated with 1.5×10⁶ *Geobacillus stearothermophilus* spores (ATCC 7953). The spores were applied to the surface of each grafted substrate using a 3 microliter suspension of spores in deionized water. The spore coated substrate was then air dried overnight at room temperature.

Assembled Biological Sterilization Indicators were exposed to vaporized hydrogen peroxide ($H_2O_2$) in a PSD-85 sterilizer (Sterilucent Incorporated., Minneapolis, Minn.) for either 0 seconds (i.e. no exposure) or 95 seconds. The devices were removed from the sterilizer and activated by pushing on the cap with enough force to break the media ampoule. The device was flicked by hand to mix and deposit the media so that it was in contact with the spore coated substrate. Fluorescence from each BI Device was measured at 60° C. using a 3M ATTEST Auto-Reader 490H (commercially available from the 3M Corporation). Fluorescence readings were taken at 30 second intervals. A positive indication for spore survival was determined as a fluorescence reading greater than or equal to 100 RFU (relative fluorescent units) above background. Three replicates were tested for each type of constructed BI device and the mean time to reach a positive detection reading was determined. The results are reported in Table 2.

TABLE 2

| BI Device with Spore Coated Substrate of | Mean Time to Reach a Positive Detection Reading for Spore Survival (RFU ≥ 100 over Background) | |
|---|---|---|
| | $H_2O_2$ Exposure for 0 seconds | $H_2O_2$ Exposure for 95 seconds |
| Example 1 | 0.5 minutes | 1.7 minutes |
| Example 2 | 1.8 minutes | 3.5 minutes |
| Example 3 | 2.0 minutes | 4.5 minutes |
| Example 4 | 0.5 minutes | 0.8 minutes |
| Example 5 | 0.5 minutes | 3.3 minutes |
| Example 6 | 1.0 minutes | 4.8 minutes |
| Example 7 | 0.5 minutes | 1.7 minutes |
| Example 8 | 0.5 minutes | 1.8 minutes |
| Comparative Example 1 | 2.0 minutes | 4.7 minutes |

All references and publications cited herein are expressly incorporated herein by reference in their entirety into this disclosure. Illustrative embodiments of this invention are discussed and reference has been made to possible variations within the scope of this invention. For example, features depicted in connection with one illustrative embodiment may be used in connection with other embodiments of the invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A method for detecting a microorganism, comprising: providing an article, the article comprising a nonwoven substrate having a copolymer grafted thereto, the copolymer comprising interpolymerized monomer units of a quaternary ammonium-containing ligand monomers, an amide monomer, and an oxy monomer; and a coating on the nonwoven substrate, the coating comprising a plurality of test microorganisms, an enzyme or a second substrate;

contacting the article with a detection medium for a period of time; and analyzing the detection medium to detect a biological activity of the test microorganisms;

wherein the quaternary ammonium-containing ligand monomer comprises [2-(Diethylamino)ethyl] methacrylate or [2-(Dimethylamino)ethyl] methacrylate.

2. The method of claim 1, wherein analyzing the detection medium to detect a biological activity of the test microorganisms comprises detecting an enzyme activity of the spores or an enzyme activity of vegetative cells derived from germination or outgrowth of a spore.

3. The method of claim 2, wherein detecting the enzyme activity comprises detecting an enzyme activity selected from the group consisting of beta-D-galactosidase, beta-D-glucosidase, alpha-D-glucosidase, alkaline phosphatase, acid phosphatase, butyrate esterase, caprylate esterase lipase, chloroamphenicol acetytransferase, catechol-2,3-dioxygenase, myristate lipase, leucine aminopeptidase, valine aminopeptidase, chymotrypsin, phosphohydrolase, alpha-D-galactosidase, alpha-L-arabinofuranosidase, N-acetyl-beta-glucosaminidase, beta-D-cellobiosidase, alanine aminopeptidase, proline aminopeptidase, tyrosine aminopeptidase, phenylalanine aminopeptidase, beta-D-glucuronidase, fatty acid esterase, and a combination of any two or more of the foregoing enzymes.

4. The method of claim 1, wherein analyzing the detection medium to detect a biological activity of the test microorganisms comprises analyzing the detection medium at a pH between 5 and 9.

5. The method of claim 1, wherein analyzing the detection medium to detect a biological activity of the test microorganisms comprises analyzing the detection medium at a pH between 6 and 8.

6. The method of claim 1, wherein contacting the article with the detection medium for a period of time comprises contacting the article with the detection medium at a predefined temperature.

7. The method of claim 1, wherein contacting the article with the detection medium for a period of time comprises contacting the article with the detection medium at a pH between 5 and 9.

8. The method of claim 1, wherein the detection medium comprises a reagent selected from the group consisting of an effective amount of a nutrient that facilitates germination or growth of the test microorganisms, an indicator compound that facilitates detection of a metabolic activity of the test microorganism, and a combination of the foregoing reagents.

9. The method of claim 8, wherein the indicator compound is selected from the group consisting of a chromogenic enzyme substrate, a fluorogenic enzyme substrate, a pH indicator, a redox indicator, a chemiluminescent enzyme substrate, a dye, and a combination of any two or more of the foregoing indicator compounds.

10. The method of claim 1, wherein the test microorganisms comprise spores.

11. The method of claim 10, wherein the spores comprise bacterial spores.

12. The method of claim 1, wherein the enzyme comprises α-glucosidase.

13. The method of claim 1, wherein the second substrate comprises 4-Methylumbelliferyl α-D-glucopyranoside.

* * * * *